United States Patent [19]

Salituro et al.

[11] Patent Number: 5,106,847
[45] Date of Patent: Apr. 21, 1992

[54] EXCITATORY AMINO ACID ANTAGONISTS, COMPOSITIONS AND USE

[75] Inventors: Francesco G. Salituro, Fairfield; Bruce M. Baron, Cincinnati, both of Ohio

[73] Assignee: Merrell Dow Pharmaceuticals Inc., Cincinnati, Ohio

[21] Appl. No.: 742,146

[22] Filed: Aug. 1, 1991

Related U.S. Application Data

[63] Continuation of Ser. No. 556,057, Jul. 16, 1990, abandoned.

[51] Int. Cl.$^5$ ............... A61K 31/405; A61K 31/535; C07D 209/18; C07D 413/12

[52] U.S. Cl. ................ 514/232.5; 514/235.2; 514/323; 514/414; 514/419; 544/80; 544/143; 546/201; 548/467; 548/468; 548/492

[58] Field of Search ............ 544/80, 143; 546/201; 548/467, 468, 492; 514/235.2, 323, 232.5, 414, 419

[56] References Cited

U.S. PATENT DOCUMENTS 4,960,786 10/1990 Salituro et al. ............ 514/419

Primary Examiner—Robert W. Ramsuer
Attorney, Agent, or Firm—J. Michael Dixon

[57] ABSTRACT

The present invention is directed a new group of indole derivatives that are NMDA antagonists.

17 Claims, No Drawings

EXCITATORY AMINO ACID ANTAGONISTS, COMPOSITIONS AND USE

CROSS-REFERENCE TO RELATED APPLICATION

This is a continuation of application Ser. No. 07/556,057, filed Jul. 16, 1990, now abandoned.

The present invention is directed to a new group of excitatory amino acid antagonists. Another aspect of the invention is directed to pharmaceutical compositions containing these compounds as well as their use in the treatment of a number of disease states.

In accordance with the present invention, a new class of excitatory amino acid antagonists have been discovered. These 4,6-disubstituted-2,3-dicarboxylic indole derivatives can be described by the following formula:

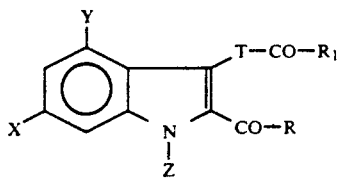

in which T is represented by a $C_{1-4}$ alkylene; Z is represented by H, $C_{1-4}$ alkyl, phenyl, substituted phenyl, or an alkylphenyl substituent in which the phenyl ring may be optionally substituted; X and Y are each independently represented by a halogen atom; R and $R_1$ are each independently represented by $-OR_2$, $-NR_3R_4$, $-OCH_2OR_2$ or $-O-(CH_2)_p-NR_5R_6$; $R_2$ is represented by hydrogen, $C_{1-4}$ alkyl, phenyl, substituted phenyl or an alkylphenyl substituent in which the phenyl ring may be optionally substituted; $R_3$ and $R_4$ are each independently represented by hydrogen or a $C_{1-4}$ alkyl; p is represented by an integer from 1-4; $R_5$ and $R_6$ are each independently represented by a $C_{1-4}$ alkyl or together with the adjacent nitrogen atom form a piperidino, morphilino, or pyrrolidinyl group; and the pharmaceutically acceptable addition salts thereof; with the proviso that at least one of $R_1$ or R must be represented by $-O-(CH_2)_p-NR_5R_6$.

As used in this application:
a) the term "halogen" refers to a fluorine, chlorine, or bromine atom;
b) the terms "lower alkyl group and $C_{1-4}$ alkyl" refer to a branched or straight chained alkyl group containing from 1-4 carbon atoms, such as methyl, ethyl, n-propyl, isopropyl, n-butyl, isobutyl, etc.;
c) the terms "lower alkoxy group and $C_{1-4}$ alkoxy" refer to a straight or branched alkoxy group containing from 1-4 carbon atoms, such as methoxy, ethoxy, n-propoxy, isopropoxy, n-butoxy, isobutoxy, etc.;
d) the term "substituted phenyl ring" refers to a phenyl moiety ($C_6H_5$) which is substituted with up to 3 substituents, each substituent is independently selected from the group consisting of halogens, $C_{1-4}$ alkyl, $C_{1-4}$ alkoxy, $CF_3$, $OCF_3$, OH, CN, and $NO_2$. These substituents may be the same or different and may be located at any of the ortho, meta, or para positions;
e) the term "alkylphenyl substituent" refers to the following structure, $-(CH_2)_m-C_6H_5$, in which m is an integer from 1-3. This phenyl ring may be substituted in the manner described immediately above;
g) the term "$C_{1-4}$ alkylene" refers to a branched or straight chained alkylene group containing from 1-4 carbon atoms, such as methylene, ethylene, n-propylene, isopropylene, n-butylene, isobutylene, etc.;
h) the term "amino ester" refers to the following substituent: $-O-(CH_2)_p-NR_5R_6$;
i) the term "functionalization reaction" refers to an esterification, amidation, etc.;
j) the term "pharmaceutically acceptable additions salt" refers to either a basic addition salt or an acid addition salt.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

Some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases, resolution via chiral salt formation and subsequent separation by selective crystallization, or enzymatic hydrolysis using stereoselective esterases as is known in the art.

As is indicated by the presence of the X and Y substituents, positions 4- and 6- of the indole ring should be substituted with a halogen atom. Positions 4- and 6- may be substituted with the same halogen atom or differing halogen atoms, (i.e., a 4,6-dichloro, a 4-bromo-6-chloro derivative, etc. should be considered within the scope of the claims).

The 2- and 3- positions of the indole ring are substituted with either a carboxylic acid or a derivative of a carboxylic acid. As noted above, at least one of these positions must be substituted with an amino ester (i.e., $-O-(CH_2)_p-NR_5R_6$). The other position may also be substituted with an amino ester or it may be substituted with one of the other carbonyl derivatives.

Z may be represented either by a substituted phenyl ring or an alkylphenyl substituent in which the phenyl ring may be substituted. One of R or $R_1$ may also be represented by a substituted phenyl ring or an alkylphenyl substituent in which the phenyl ring may be substituted. Any of these phenyl rings may contain up to 3 substitutents which may be located at any of the ortho, meta, or para positions. Each phenyl ring may be substituted with the same substituents or differing substituents. The specific substitutions may be any of those listed above in the definition of substituted phenyl ring.

T is represented by a $C_{1-4}$ alkylene. This $C_{1-4}$ alkylene may be either linear or branched. $R_3$ and $R_4$ may be represented by the same substituent or differing substitutents. Likewise $R_5$ and $R_6$ may be represented by the same substitutent or differing substitutents.

Illustrative examples of compounds encompassed by formula I include:
a) 2-dimethylaminoethyl-3-[2-(2-dimethylaminoethoxycarbonyl) -4,6-dichloroindol-3-yl]propionate,
b) 2-diethylaminoethyl-3-[2-(2-diethylaminoethoxycarbonyl)-4,6-dichloroindol-3-yl]propionate,
c) 2-(4-morpholinyl)ethyl-3-[2-(2-(4-morpholinyl)ethoxycarbonyl)-4,6-dichloroindol-3-yl]propionate,
d) 2-(4-piprizinyl)ethyl-3-[2-(2-(4-piprizinyl)ethoxycarbonyl) -4,6-dichloroindol-3-yl]propionate,
e) 2-(1-pyrrolidinyl)ethyl-3-[2-(2-(1-pyrrolidinyl) ethoxycarbonyl)-4,6-difluoroindol3-5 yl]propionate,
f) 3-[2-(2-dimethylaminoethoxycarbonyl)-4,6-dichloroindol-3-yl]propionic acid, and
g) 2-dimethylaminoethyl-3-[2-carboxy-4,6-dichloroindol-3-yl]propionate.

It is preferred for T to be represented by an ethylene group.

The compounds of Formula I can be prepared utilizing techniques that are analogously known in the art. One method of preparing these compounds is disclosed below in Reaction Scheme I:

REACTION SCHEME I

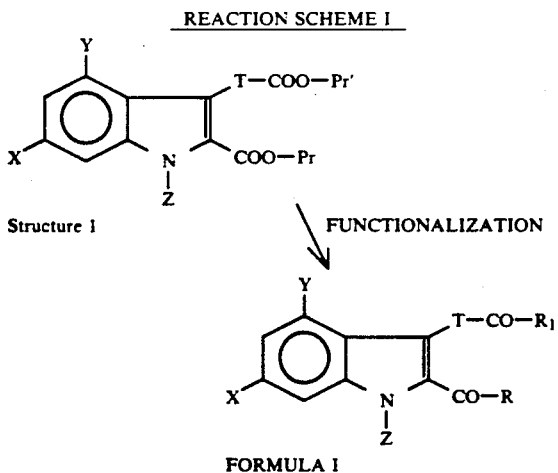

Structure 1

FUNCTIONALIZATION

FORMULA I

As is disclosed in Reaction Scheme I, the compounds of Formula I can be prepared by submitting one of the 4,6-di-substituted-indoles of Structure 1 to an appropriate functionalization reaction which introduces the appropriate functionality at the 2- and/or 3-positions of the indole nucleus thereby producing one of the desired compounds of Formula I. In structure (1), X, Y, T and Z are as in Formula I and Pr and Pr' are each independently represented by groups such as hydrogen, a $C_{1-4}$ alkyl, or other active ester leaving groups known in the art. The appropriate indole of structure 1 to utilize as a starting material is one in which X, Y, T and Z are represented by the same substituents as is desired in the final product of Formula I. The exact identity of the Pr and Pr' leaving groups are immaterial since they will not be retained in the final product.

The functionalization reactions can be carried out using techniques well known in the art. For example ester functionalities can be added to the 2- and/or 3-positions of the indole nucleus of structure 1 utilizing a variety of esterification techniques. One suitable esterification technique comprises contacting the appropriate compound of structure 1 in which Pr and Pr' are $C_{1-4}$ alkyl functions with an excess of an alcohol of the formula ROH, in which R is the same as in Formula I and is represented by the same functionality as is desired in the final product (esterification technique #1). The reaction is typically carried out in the presence of an excess of a base such as potassium carbonate. The reaction is typically carried out at a temperature ranging from room temperature to reflux for a period of time ranging from 1 hour to 24 hours. After the reaction is completed, the desired product of Formula I can be recovered by organic extraction. It may then be purified by flash chromatography and/or recrystallization as is known in the art. Suitable chromatagraphic solvents include 5% methanol in trichloromethane. Suitable recrystallization solvents include ethyl acetate/hexane.

Another suitable esterification techniques comprises contacting a compound according to structure 1 in which Pr and Pr' are represented by H with an excess of an alcohol of the formula ROH, in which R is the same as in Formula I and is represented by the same functionality as is desired in the final product (esterification technique #2). The reaction is typically carried out in the presence of an excess amount of triphenylphosphine and an excess amount of diethyldiazodicarboxylate (DEAD). The reaction is typically carried out at a temperature range of from 25° C. to 35° C. for a period of time ranging from 1 to 6 hours. The desired product of Formula I can be recovered and purified as taught above.

Amides can also be easily be prepared by contacting a compound of structure 1 in which Pr and Pr' are $C_{1-4}$ alkyls with an excess of ammonia or a mono- or dialkylamine corresponding to the desired R or $R_1$ substituent at a temperature of from 0°–100° C. for a period of time ranging from 1-48 hours in an inert solvent such as tetrahydrofuran. The resulting amide derivatives of Formula I can then be isolated and purified by techniques known in the art.

As is readily apparent to those skilled in the art, if R and $R_1$ are not both represented by the same function in the final product, then it will be necessary to carry out the functionalization reactions in a sequential manner utilizing suitable protecting groups such as those described in *Protecting Groups in Organic Synthesis* by T. Greene. This can be done utilizing techniques known to those skilled in the art.

One suitable sequential esterification technique is depicted below in Reaction Scheme II.

REACTION SCHEME II

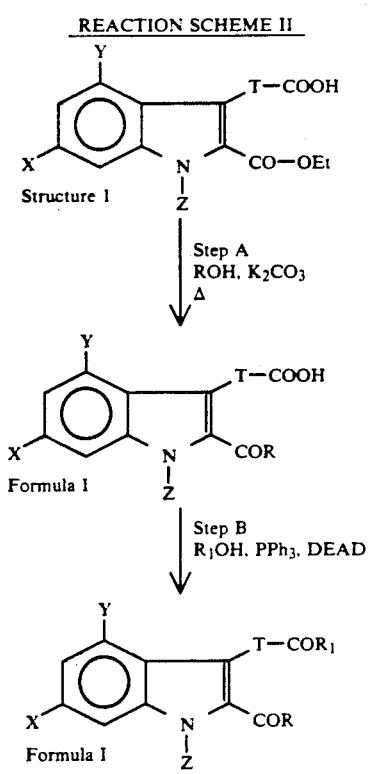

In Step A, the indole derivative of Structure 1 in which X, Y, Z and T are as above and Pr is ethyl while Pr' is H as depicted, is subjected to a transesterification reaction which introduces the desired ester moiety at the 2-position of the indole nucleus. This transesterification is carried out in the same manner as that taught above for esterification technique #1. The resulting product can be recovered and purified as taught in Reaction Scheme I. In Step B the desired ester moiety is introduced into the 3-position of the indole nucleus. This can be accomplished by subjecting the product of Step A to an esterification reaction using the techniques taught above for esterification technique #2. The resulting product may also be recovered and purified as taught in Reaction Scheme I. Other sequential reactions known to those skilled in the art are also equally suitable.

The 4-6-disubstituted indole starting material of structure 1 can be prepared utilizing techniques known in the art For example see:
1) T. Nagasaka, S. Ohki, *Chem. Pharm. Bull.*, 25 (11), 3023-3033 (1977).
2) R. E. Bowman, T. G. Goodburn, A. A. Reynolds, *J. Chem. Soc. Perkin Trans.* 1, 1121-1123 (1972).
3) M. D. Meyer, L. I. Kruse, *J. Org. Chem.*, 49, 3195-3199 (1984).
4) British Patent 1,004,661, Sep. 15, 1965.
5) M. Rensen, *Bull. Soc. Chim., Belges*, 68, 258-269 (1959).
6) W. Reid, A. Kleemann, *Justus Liebigs Ann. Chem.*, 713, 127-138 (1968).

The compounds of Formula I are excitatory amino acid antagonists. They antagonize the effects which excitatory amino acids have upon the NMDA receptor complex. They preferentially bind to the strychnine-insensitive glycine binding site associated with the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, autonomic seizures, etc. One method of demonstrating their anti-epileptic properties is by their ability to inhibit the seizures that are caused by the administration of quinolinic acid. This test can be conducted in the following manner.

One group containing ten mice are administered 0.01-100 $\mu$g of test compound intraperitoneally in a volume of 5 microliters of saline. A second control group containing an equal number of mice are administered an equal volume of saline as a control. Approximately 5 minutes later, both groups are administered 7.7 micrograms of quinolinic acid intraperitoneally in a volume of 5 microliters of saline. The animals are observed for 15 minutes thereafter for signs of clonic seizures. The control group will have a statistically higher rate of clonic seizures than will the test group.

Another method of demonstrating the anti-epileptic properties of these compounds is by their ability to inhibit audiogenic convulsions in DBA/2 mice. This test can be conducted in the following manner. Typically one group of from 6-8 male DBA/2J audiogenic susceptible mice are administered from about 0.01 $\mu$g to about 10 $\mu$g of the test compound. The test compound is administered intracerebrally into the lateral ventricle of the brain. A second group of mice are administered an equal volume of a saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

The compounds of Formula I are useful for preventing or minimizing the damage which nervous tissues contained within the CNS suffer upon exposure to either ischemic, traumatic, hypoxic, or hypoglycemic conditions. Representative examples of such ischemic, hypoxic, traumatic, or hypoglycemic conditions include strokes or cerebrovascular accidents, concussions, hyperinsulinemia, cardiac arrest, drownings, suffocation, and neonatal anoxic trauma. The compounds should be administered to the patient within 24 hours of the onset of the hypoxic, ischemic, traumatic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, physical injury, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., Distress vocalization in rat pups: a simple screening method for anxiolytic drugs. *J. Pharmacol. Methods*, 14:181-187 (1985) and Insel et al. Rat pup ultrasonic isolation calls: Possible mediation by the benzodiazepine receptor complex. *Pharmacol. Biochem. Behav.*, 24: 1263-1267 (1986).

The compounds also exhibit an analgesic effect and are useful in controlling pain.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

As used in this application:
a) the term "patient" refers to warm blooded animals such as, for example, guinea pigs, mice, rats, cats, rabbits, dogs, monkeys, chimpanzees, and humans;
b) the term "treat" refers to the ability of the compounds to either relieve, alleviate, or slow the progression of the patient's disease;
c) the term "neurodegeneration" refers to a progressive death and disappearance of a population of nerve cells occurring in a manner characteristic of a particular disease state and leading to brain damage.

The compounds of Formula I may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formula I may be utilized in diagnostic procedures to aid physicians with the diagnosis of neurodegenerative diseases. The compounds may be labelled with imaging agents known in the art such as isotopic ions and administered to a patient in order to determine whether the patient is exhibiting a decreased number of NMDA receptors and the rate at which that loss is occurring.

The following Examples are being presented in order to further illustrate the invention. They should not be construed as limiting the invention in any manner.

EXAMPLE 1

2-Dimethylaminoethyl-3-[2-(2-dimethylaminoethoxycarbonyl)-4,6-dichloroindol-3-yl]propionate Ethyl 3-(2-carboxyethyl-4,6-dichloroindol-3-yl)propionate (0.4 g, 1.12 mmol) was dissolved in dimethylaminoethanol (2 ml). To this solution was added potassium carbonate (2.31 g, 2.24 mmol). The reaction flask was sealed and heated at 70° C. with vigorous stirring. After 24 h, the reaction mixture was cooled to room temperature, filtered, and diluted with ethyl acetate (75 ml). The organic layer was washed with water and saturated NaCl, dried (MgSO$_4$) and concentrated in vacuo. The residue was applied to a silica gel flash column and eluted with 5% CH$_3$OH/CHCl$_3$. Subsequent recrystallization of the isolated product (ethyl acetate/hexane) gave colorless crystals (220 mg, 44%) m.p. 95°-97° C.; NMR (CDCl$_3$) S 2.29 (s, 6H), 2.32 (s, 6H), 2.55-2.65 (m, 4H), 2.71 (t, J=Hz, 2 H), 3.55-3.65 (m, 2H), 4.19 (t, J=7 Hz, 2 H), 4.44 (t, J=7 Hz, 2 H), 7.08 (s, 1 H), 7.22 (s, 1 H), 10.3 (broad m, 1H). Analysis calculated for C$_{20}$H$_{27}$Cl$_2$N$_3$O$_4$: C, 54.06; H, 6.12; N, 9.46. Found: C, 53.97; H, 6.07; N, 9.38.

EXAMPLE 2

2-(4-Morpholinyl)ethyl-3-[2-(2-(4-morpholinyl)ethoxycarbonyl)4,6-dichloroindol-3-yl]propionate To 0.65 g (4.97 mmol) of 2-N-morpholinoethanol and 0.96 g (3.64 mmol) of triphenylphosphine in 10 mL of dry THF was added dropwise 0.50 g (1.66 mmol) of 3-(2-carboxy-4,6-dichloroindol-3-yl)propionic acid and 0.63 g (3.64 mmol) of diethylazodicarboxylate (DEAD)

in 10 mL of THF. After 5 hours, the THF was evaporated and the resulting colorless oil was taken up in 50 mL of $CH_2Cl_2$. Silica gel was added to the solution and evaporation of the solvent afforded the crude product absorbed onto the silica gel. This was added to a flash column and eluted with 1% methanol in chloroform solution resulting in the separation of 2-(4-morpholinyl)ethyl-3-[2-(2-(4-morpholinyl) ethoxycarbonyl)-4,6-dichloroindol-3-yl]propionate from triphenylphosphine oxide and dihydrodiethylazodicarboxylate. Evaporation of the solvent gave 0.68 g (78% yield) of 2-(4-morpholinyl)ethyl-3-[2-(2-(4-morpholinyl) ethoxycarbonyl)-4,6-dichloroindol-3-yl]propionate as a white solid. This material was recrystallized from a mixture of ethylacetate and hexanes to give 0.54 g (62% yield) of 2-(4-morpholinyl)ethyl-3-[2-(2-(4-morpholinyl) ethoxycarbonyl)-4,6-dichloroindol-3-yl]propionate as white crystalline material, mp 110°-112° C., $^1$HNMR ($CDCl_3$) ppm 2.50 (2 H, t), 2.55-2.75 (10 H, m), 2.8 (2 H, t) 3.65-3.80 (10 H, m), 4.25 (2 H, t, $CH_2$—O—CO), 4.50 (2 H, t, $CH_2$—O—CO), 7.15 (1 H, s, ArH), 7.35 (1 H, s, ArH), 9.45 (1 H, bs, NH).

EXAMPLE 3

2-Diethylaminoethyl-3-[2-(2-diethylaminoethoxycarbonyl)-4,6-dichloroindol-3-yl]propionate The method described in the preparation of 2-(4-morpholinyl)ethyl-3-[2-(2-(4-morpholinyl) ethoxycarbonyl)-4,6-dichloroindol-3-yl]propionate was utilized in the synthesis of 2-diethylaminoethyl-3-[2-(2-diethylaminoethoxycarbonyl)-4,6-dichloroindol-3-yl]propionate using 0.21 g (2.40 mmol) of diethylaminoethanol, 0.46 g (1.76 mmol) of triphenylphosphine, 0.24 g (0.80 mmol) of 3-(2-carboxy-4,6-dichloroindol-3-yl)propionic acid, and 0.31 g (1.76 mmol) of DEAD. After flash chromatography, 0.24 g (61% of 2-diethylaminoethyl-3-[2-(2-diethylaminoethoxycarbonyl)-4,6-dichloroindol-3-yl]propionate was isolated as a pale yellow oil.

$^1$HNMR ($CDCl_3$) ppm 1.10 (12 H, t, —$CH_3$), 2.50-2.75 (12 H, m), 2.89 (2 H, t, —$CH_2$—$NEt_2$), 2.70 (2 H, t, $CH_2$), 4.15 (2 H, t, $CH_2$—O—CO), 4.45 (2 H, t, $CH_2$—O—CO), 7.05 (1 H, s, ArH), 7.25 (1 H, s ArH), 10.35 (1 H, s, —NH).

What is claimed is:

1. A compound of the formula:

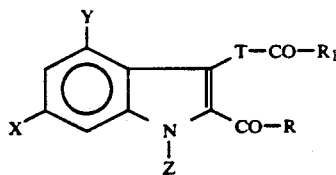

in which T is represented by a $C_{1-4}$ alkylene; Z is represented by H, $C_{1-4}$ alkyl, phenyl, substituted phenyl, or an alkylphenyl substituent in which the phenyl ring may be optionally substituted; X and Y are each independently represented by a halogen atom; R and $R_1$ are each independently represented by —$OR_2$, —$NR_3R_4$, —$OCH_2OR_2$ or —O—$(CH_2)_p$—$NR_5R_6$; $R_2$ is represented by hydrogen, $C_{1-4}$ alkyl, phenyl, substituted phenyl or an alkylphenyl substituent in which the phenyl ring may be optionally substituted; $R_3$ and $R_4$ are each independently represented by hydrogen Or a $C_{1-4}$ alkyl; p is represented by an integer from 1–4; $R_5$ and $R_6$ are each independently represented by a $C_{1-4}$ alkyl or together with the adjacent nitrogen atom for a piperidino, morphilino, or pyrrolidinyl group; and the pharmaceutically acceptable addition salts thereof; with the proviso that at least one of $R_1$ or R must be represented by —O—$(CH_2)_p$—$NR_5R_6$.

2. A compound according to claim 1 wherein T is ethylene.

3. A compound according to claim 1 wherein R and $R_1$ are both represented by —O—$(CH_2)_p$—$NR_5R_6$.

4. A compound according to claim 1 in which said compound is 2-dimethylaminoethyl-3-[2-(2-dimethylaminoethoxycarbonyl)-4,6-dichloroindol-3-yl]propionate.

5. A compound according to claim 1 in which said compound is 2-diethylaminoethyl-3-[2-(2-diethylaminoethoxycarbonyl)-4,6-dichloroindol-3-yl]propionate.

6. A compound according to claim 1 in which said compound is 2-(4-morpholinyl)ethyl-3-[2-(2-(4-morpholinyl) ethoxycarbonyl)-4,6-dichloroindol-3-yl]propionate.

7. A compound according to claim 1 in which said compound is 2-(1-pyrrolidinyl)ethyl-3-[2-(2-(1-pyrrolidinyl) ethoxycarbonyl)-4,6-difluoroindol-3-yl]propionate.

8. A compound according to claim 1 in which said compound is 3-[2-(2-dimethylaminoethoxycarbonyl)-4,6-dichloroindol-3-yl]propionic acid.

9. A compound according to claim 1 in which said compound is 2-dimethylaminoethyl-3-[2-carboxy-4,6-dichloroindol-3-yl]propionate.

10. A method for antagonizing the effects of excitatory amino acids upon the NMDA receptor complex comprising administering to a patient in need thereof, an antagonistic amount of a compound according to claim 1.

11. A method for the treatment of epilepsy comprising administering to a patient in need thereof an anti-epileptic amount of a compound according to claim 1.

12. A method for the treatment of neurodegenerative diseases comprising administering to a patient in need thereof an effective amount of a compound according to claim 1.

13. A method for preventing ischemic/hypoxic/hypoglycemic damage to cerebral tissue comprising administering to a patient in need thereof an effective amount of a compound according to claim 1.

14. A method for the treatment of anxiety comprising administering an anxiolytic amount of a compound according to claim 1.

15. A method for producing an analgesic effect comprising administering to a patient in need thereof an analgesic amount of a compound according to claim 1.

16. A composition comprising a compound according to claim 1 in admixture with an inert carrier.

17. A composition according to claim 16 wherein said inert carrier is a pharmaceutically acceptable carrier.

* * * * *

UNITED STATES PATENT AND TRADEMARK OFFICE
CERTIFICATE OF CORRECTION

PATENT NO. : 5,106,847
DATED : April 21, 1992
INVENTOR(S) : Francesco G. Salituro and Bruce M. Baron It is certified that error appears in the above-identified patent and that said Letters Patent is hereby corrected as shown below:

```
At Column 3, Line 35 the patent reads:
   "difluoroindol3-5  yl" and should read:
    --difluoroindol-3-yl--.

At Column 8, Line 62 the patent reads:
   "ethoxycarbonyl)4,6-dichloroindol" and should read:
   --ethoxycarbonyl)-4,6-dichloroindol--.

At Column 9, Line 7 the patent reads:
   "(4-morpholinyl-)ethyl-3" and should read:
   --(4-morpholinyl)-ethyl-3--.
```

Signed and Sealed this

Tenth Day of August, 1993

Attest:

MICHAEL K. KIRK

*Attesting Officer*     Acting Commissioner of Patents and Trademarks